(12) United States Patent
Bush et al.

(10) Patent No.: US 8,388,531 B2
(45) Date of Patent: *Mar. 5, 2013

(54) METHODS AND SYSTEMS FOR ASSESSING GASTRIC EMPTYING

(75) Inventors: Kerry C. Bush, Brentwood, TN (US); Robert F. Martin, Missouri City, TX (US)

(73) Assignee: Advanced Breath Diagnostics, LLC, Brentwood, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/443,151

(22) Filed: Apr. 10, 2012

(65) Prior Publication Data

US 2012/0197116 A1 Aug. 2, 2012

Related U.S. Application Data

(62) Division of application No. 12/116,423, filed on May 7, 2008.

(60) Provisional application No. 61/016,011, filed on Dec. 21, 2007, provisional application No. 60/917,202, filed on May 10, 2007.

(51) Int. Cl.
*A61B 5/00* (2006.01)
*A61B 8/00* (2006.01)
*A61B 5/08* (2006.01)
*A61K 51/00* (2006.01)
(52) U.S. Cl. ........ 600/300; 600/436; 600/532; 424/1.17
(58) Field of Classification Search .................. 600/300, 600/436, 532; 424/1.17
See application file for complete search history.

(56) References Cited

U.S. PATENT DOCUMENTS

| | | | |
|---|---|---|---|
| 4,985,232 A | 1/1991 | Jacobssen | |
| 5,140,993 A | 8/1992 | Opekun | |
| 5,233,997 A | 8/1993 | Klein | |
| 5,707,602 A | 1/1998 | Klein | |
| 5,785,949 A | 7/1998 | Klein | |
| 6,273,854 B1 | 8/2001 | Kane | |
| 6,432,382 B1 | 8/2002 | Mehta | |
| 6,548,043 B1 | 4/2003 | Wagner | |
| 6,740,305 B1 | 5/2004 | Ajami | |
| RE38,728 E | 4/2005 | Katzman | |
| 7,785,569 B2 | 8/2010 | Evans | |
| 2002/0011250 A1 | 1/2002 | Stewart | |
| 2007/0014718 A1 | 1/2007 | Lee | |
| 2008/0033253 A1 | 2/2008 | Neville | |
| 2008/0281193 A1 | 11/2008 | Ben Oren | |
| 2008/0286200 A1 | 11/2008 | Bush | |
| 2010/0241606 A9 | 9/2010 | Wanger | |

FOREIGN PATENT DOCUMENTS

| | | |
|---|---|---|
| GB | 2360845 | 10/2001 |
| WO | 97/35622 | 10/1997 |
| WO | 01/72342 | 10/2001 |

OTHER PUBLICATIONS

Pellegrini et al., Diagnosis and Treatment of Gastric Emptying Disorders. American Journal of Surgery 145 : 143 (1983).*
Bouras et al., Gastric Motility disorders :Management that Optimizes Nutritional Status. Journal of Clinical Gasteroenterology 38 (7) : 549 (2004).*
J S Lee, et al., "A Valid, Accurate, Office Based Non-Radioactive Test for Gastric Emptying of Solids" Gut 2000; 46:768-773.
B.E. Viramontes, et al., "Validation of a Stable Isotope Gastric Emptying Test for Normal, Accelerated or Delayed Gastric Emptying" Neurogastroenterol. Mot. (2001) 13, 567-574.
Yvo F. Ghoos, et al., "Measurement of Gastric Emptying Rate of Solids by Means of a Carbon-Labeled Octanoic Acid Breath Test" Gastroenterology 1993;104:1640-1647.
International Search Report and Written Opinion, dated Apr. 8, 2008 for PCT Application No. PCT/US08/62840, 10 pages.
Abell et al., "Treatment of gastroparesis: a multidisciplinary clinical review", Neurogastroenterol Motil (2006) 18, 263-283.
B. Rosner, On the Detection of Many Outliers, Technometrics, 17/2, 221-227 (1975).
Breidthardt et al., "Medical and Economic Long-term Effects of B-type Natriuretic Peptide Testing in Patients with Acute Dyspnea", Clinical Chemistry 53:8 (2007), 1415-1422.
Bytzer et al., "GI Symptoms in Diabetes Mellitus are Associated with Both Poor Glycemic Control and Diabetic Complications" Am J Gastroenterology; 2002, vol. 97, No. 3, pp. 604-611.
Bytzer et al., "Prevalence of gastrointestinal symptoms associated with diabetes mellitus: a population-based survey of 15,000 adults," Arch Intern Med 2001; 161:1989-1996.
Chamorro et al., "Pharmacology and toxicology of *Spirulina alga*," Rev Invest Clin Sep.-Oct. 1996; 48(5):389-99.
Chamorro et al., "Subchronic toxicity study in rats fed *Spirulina*," J. Pharm Belg., 1988, 43, 1, 29-36.
Ciferri et al., "Spirulina the Edible Microorganism," Microbiological Reviews, Dec. 1983, p. 551-578.
Coste et al., "A Gray Zone Assigned to Inconclusive Results of Quantitative Diagnostic Tests: Application to the Use of Brain Natriuretic Peptide for Diagnosis of Heart Failure in Acute Dyspneic Patients", Clinical Chemistry 52:12 (2006), 2229-2235.
Enck et al., "Prevalence of gastrointestinal symptoms in diabetic patients and non-diabetic subjects," Z Gastroenterol 1994; 32:637-641.
FDA Talk Paper, "*Spirulina*", Jun. 23, 1981.
Feinstein, "The inadequacy of binary models for the clinical reality of three-zone diagnostic decisions", J Clin Epidemiol, 43, 109-113 (1990).
Harris, et al., Statistical Bases of Reference Values in Laboratory Medicine, Marcel Dekker, 1995, Chapter 8: Analytical Goals for Reference Values.
Janatuinen et al., "Gastrointestinal symptoms in middle-aged diabetic patients," Scan J Gastroenterol 1993; 28:427-432.

(Continued)

*Primary Examiner* — Ethan C Whisenant
(74) *Attorney, Agent, or Firm* — Fredrikson & Byron, P.A.

(57) ABSTRACT

Gastric emptying classification systems, displays, methods for classifying gastric emptying data, methods for treating patients, and methods for developing gastric emptying classification systems are disclosed.

15 Claims, 5 Drawing Sheets

OTHER PUBLICATIONS

Krishnakumari et al., "Food safety evaluation: acute oral and dermal effects of the algae *Scenedesmus acutus* and *Spirulina platensis* on albino rats", J. of Food Protection, vol. 44, No. 12, Dec. 1981, 934-935.

Lidums et al., "Effect of atropine on proximal gastric motor and sensory function in normal subjects", Gut 2000; 47:30-6.

Maleki et al., "Gastrointestinal tracts symptoms among persons with diabetes mellitus in the community," Arch Intern Med 2000; 160:2808-2816.

Park et al., "Clinical Reviews: Gastroparesis: Clinical Update" American Journal of Gastroenterology, ISSN 0002-9270 (2006), 1129-1139.

R.S. Chhikara et al, Extended critical Values of Extreme Studentized Deviate Test Statistics for Detecting Multiple Outliers, Commun. Statist.-Simula. Computa., B9(2), 155-166 (1980).

Salazar et al., "Effect of *Spirulina maxima* consumption on reproduction and peri- and postnatal development in rats," Food and Chemical Toxicology, 34 (1996) 353-359.

Schofield, "Predicting basal metabolic rate, new standards and review of previous work", Hum Nutr Clin Nutr (1985) 39, 541.

Solberg, "RefVal: a program implementing the recommendations of the International Federation of Clinical Chemistry on the statistical treatment of reference values", Computer Methods and Programs in Biomedicine 1995, 48:247-256.

Szarda et al. "A Stable Isotope Breath Test with a Standard Meal for Abnormal Gastric Emptying of Solids in the Clinic and in Research", Clinical Gastroenterology and Hepatology, 2008; 6:635-643.

Talley et al., "Effects of a motilin receptor agonist (ABT-229) on upper gastrointestinal symptoms in type 1 diabetes mellitus: a randomized, double-blind, placebo controlled trial," Gut 2001; 49:395-401.

Talley et al., "Epidemiology of colonic symptoms and the irritable bowel syndrome," Gastroenterology 101:927-934, 1991.

Taub et al, "Irritable bowel syndrome defined by factor analysis. Gender and race comparisons." Dig Dis Sci 40:2647-2655, 1995.

Yoshino et al., "The chronic intoxication test of *Spirulina* product fed to wistar rats," Japanese Journal of Nutrition, 38 (5), 1980, 221-226.

Zuckerman et al., "Healthcare-seeking behaviors related to bowel complaints. Hispanics versus non-Hispanic whites." Dig Dis Sci 41:77-82, 1996.

Bytzer et al., "Gastrointestinal symptoms in Diabetes Mellitus are Associated with Diabetic Complications but not with Current Glycemic Control," Abstract from Digestive Disease Week (DDW) 2000; Gastroenterology 2000; 118:A468.

Bjorkman et al., The Am. J. of., Gasteroenterology 86 (7): 821-823 (1991).

Choi et al. Gasteroenterology 112(4): 1155-1162 (1997)—Abstract only.

Donohoe et al., J. of Nuc. Med. 40(7): 1236-1239 (1999).

Ducrot et al. Digestive Diseases and Sciences 34(5): 657-664 (1989).

Parkman et al., Gasteroenterology 127(5): 1592-1622 (2004).

* cited by examiner

METHODS AND SYSTEMS FOR ASSESSING GASTRIC EMPTYING

CROSS REFERENCE TO RELATED APPLICATIONS

This application is a divisional application of U.S. patent application Ser. No. 12/116,423, filed May 7, 2008, which in turn claims priority to U.S. provisional patent application No. 61/016,011, filed Dec. 21, 2007, which in turn claims priority to U.S. provisional patent application No. 60/917,202, filed May 10, 2007, the entire contents of each of which are incorporated herein by reference.

BACKGROUND

The processing and utilization of food generally involves five functions accomplished by the digestive tract. They include motility, secretory, digestive absorptive and elimination functions. Processing of food begins in the oral cavity where food is mechanically broken down by mastication, lubricated with saliva, and enzymatically processed by amylase present in the saliva. Processing continues in the stomach where food is liquefied by gastric juices and enzymes secreted by the cells lining the stomach to produce chyme. Chyme enters the small intestine via the pyloric sphincter for further processing by bile salts produced by the liver and digestive enzymes produced by the pancreas. The small intestine absorbs most components from chyme through its walls, and the large intestine subsequently processes components that are not absorbed by the small intestine. Finally, the large intestine propels waste products into the colon, where they remain, usually for a day or two, until the feces are expelled by a bowel movement.

Sometimes, a person takes an abnormally long time to process and digest food, or a person may process food too quickly. This abnormal gastrointestinal function can be contributed to a disorder that affects the digestive tract, whether it be a disorder in the stomach or a disorder beyond the stomach. Commonly, a disorder occurs in the stomach that causes food to be emptied from the stomach into the small intestine too quickly or after too long of a time. Stomach emptying disorders ("dysmotility") can be diagnosed by measuring the rate at which a meal empties from the stomach and enters the small intestine (the "gastric emptying rate"). When the rate is accelerated, ingested food is prematurely dumped from the stomach to the small intestine, giving rise to the condition termed "rapid emptying" or otherwise known as the dumping syndrome. Conversely, when the rate is decelerated, the movement of ingested food from the stomach to the small intestine is delayed, giving rise to the condition termed "delayed emptying" otherwise known as gastroparesis.

Two known tests for measuring gastric emptying rates are quantitative scintigraphy tests and gastric emptying breath tests ("GEBT"). In scintigraphy testing, a patient ingests a meal including at least one edible food, a component of which has been radiolabeled. The gamma emission from the radiolabel is measured by a scintillation camera as the labeled food is emptied from the stomach. Scintigraphy measurements of gastric emptying are direct, since the camera directly measures the gamma emissions arising from the radiolabeled meal remaining in the stomach. In breath testing, a patient ingests a meal that includes a non-radioactive marker or label, e.g., carbon-13 ($^{13}C$), a stable, non-radioactive isotopic form of carbon. As the non-radioactive labeled edible food is processed by the digestive tract, a labeled component, e.g., $^{13}CO_2$, is produced which can be detected in the patient's breath. In contrast to scintigraphy, measurement of gastric emptying using breath testing is indirect. Results for both types of testing are interpreted as either positive (abnormal) or negative (normal) for either gastroparesis or for accelerated emptying. Test results are therefore viewed from a dichotomous point of view.

SUMMARY

Certain embodiments provide a diagnostic gastric emptying classification system including an abnormal zone, a borderline zone, and a normal zone, wherein the abnormal zone is either a delayed emptying zone or a rapid emptying zone, wherein each the abnormal zone, the borderline zone, and the normal zone have been developed using gastric emptying measurements from healthy patients and measurements of normal day-to-day within-subject biologic variation in healthy subjects and moderately impaired subjects.

Other embodiments provide a display for illustrating gastric emptying results, the display including a series of time points and a gastric emptying classification system associated with each time point in said series of time points, the gastric emptying classification system comprising an abnormal zone, a borderline zone, and a normal zone, wherein the abnormal zone is a delayed emptying zone or a rapid emptying zone.

Further embodiments provide a method for assessing a patient's gastric emptying function, the method including performing a gastric emptying test on the patient, obtaining a gastric emptying measurement for at least one desired time point, classifying the gastric emptying measurement, the classifying comprising placing the gastric emptying measurement into a diagnostic zone selected from the group consisting of an abnormal zone, a borderline zone, or a normal zone, wherein the abnormal zone is either a delayed emptying zone or a rapid emptying zone, and wherein each the abnormal zone, the borderline zone, and the normal zone have been developed using gastric emptying measurements from healthy patients and measurements of normal day-to-day biologic variation of gastric emptying in healthy subjects and moderately impaired subjects.

Other embodiments provide a method of treating a patient, including performing a gastric emptying test on the patient, obtaining a gastric emptying measurement at a desired time point, classifying said gastric emptying measurement at said desired time point, the classifying comprising placing the gastric emptying measurement in one or more diagnostic zones selected from the group consisting of an abnormal zone, a borderline zone, and a normal zone, wherein the abnormal zone is either a delayed emptying zone or a rapid emptying zone, and wherein the borderline zone is either a delayed emptying borderline zone or a rapid emptying borderline zone, and selecting a level of therapeutic action that is appropriate for the selected zone. The selecting can include selecting no action when the normal zone is selected, selecting a delayed emptying mild action or a delayed emptying aggressive action when the delayed emptying borderline zone is selected, selecting a rapid emptying mild action or a rapid emptying aggressive action when the rapid delayed emptying borderline zone is selected, selecting a delayed emptying aggressive action or a delayed emptying very aggressive action when the delayed emptying zone is selected, or selecting a rapid emptying aggressive action or a rapid emptying very aggressive action when the rapid emptying zone is selected.

Even other embodiments provide a method for developing a gastric emptying zone classification system, the method including performing gastric emptying tests on a series of healthy patients, obtaining gastric emptying measurements for the series of healthy patients at a desired time point, using said gastric emptying measurements to form a reference interval for said desired time point, using an upper fractile or a lower fractile bound of the reference interval as a cutoff point for demarcating normal gastric emptying measurements from abnormal gastric emptying measurements, measuring day to day within-subject biologic variation for the series of healthy patients and modestly impaired patients at the desired time point to obtain within-subject biologic variation measurements, and calculating a normal zone, a borderline zone, and an abnormal zone, the borderline zone being calculated around the cutoff point using the within-subject biologic variation measurements.

BRIEF DESCRIPTION OF THE FIGURES

FIG. 2a is one embodiment of a display of patent classification into delayed emptying, delayed emptying borderline, and normal at certain testing time points;

FIG. 2b is one embodiment of a display of patient classification into rapid emptying, rapid emptying borderline, and normal, at certain testing time points;

FIG. 2c is one embodiment of a display of patient classification into rapid emptying, rapid emptying borderline, normal, delayed emptying borderline, and delayed emptying at certain testing time points;

DETAILED DESCRIPTION

Applicant has performed extensive studies using known gastric emptying methods and has discovered that gastric emptying measurements are best classified according to a zone approach, rather than a dichotomous (simply positive or negative) approach. Persons of skill in the art have not thought to use a zone approach as diagnostic results regarding gastric emptying measurements have historically and universally been classified dichotomously, and the problems associated with dichotomous testing and the advantages of using a polychotomous zone approach were not known. Furthermore, previous studies have not revealed enough data to show that a zone approach would work best and it was unknown how such zones should be determined.

Unlike most other diagnostic tests, measurements of gastric emptying exhibit complex problems not heretofore addressed. First, the distribution of gastric emptying rates observed in patients with gastric dysmotility, e.g. patients symptomatic for delayed gastric emptying, vs. healthy, normal, reference subjects are overlapping and do not form separate independent distributions. This creates complexity and uncertainty in differentiating those with and without disease. Secondly, diagnostic classification is further complicated by significant, natural, within-subject, day-to-day biologic variation that occurs in gastric emptying physiology. The later is superimposed on the former creating a complex interpretive problem.

Applicant has discovered that measurement of gastric emptying rates (for example, either by breath testing or scintigraphy testing) in patients symptomatic for gastric dysmotility, e.g., gastroparesis, yields a unimodal distribution of emptying rates ranging from 0 to rates consistent with those observed in healthy non-compromised patients, and even higher. This unimodal roughly Gaussian distribution of patient values completely overlaps with the distribution of values observed in healthy (reference) subjects, which, in itself, is also unimodal and roughly Gaussian in nature. In this situation, it is not appropriate to simply dichotomize results into two simple categories—positive or negative. However, dichotomous classification (positive or negative) is completely appropriate when the frequency distributions of test results for diseased vs. not diseased subjects are distinctly separated. For example, patients infected with the bacterium *Helicobacter pylori* may be tested for the infection by a $^{13}$Carbon breath test (the $^{13}$C-Urea Breath Test for *H. pylori*). The breath test values for infected vs. non-infected subjects yield completely separate distributions and have no overlap. Another example is pregnant vs. non-pregnant subjects. Because these distributions do not overlap, use of a simple cutoff point can unambiguously classify these patients as either positive or negative. Such is not the case for gastric emptying measurements.

Figure 1A:
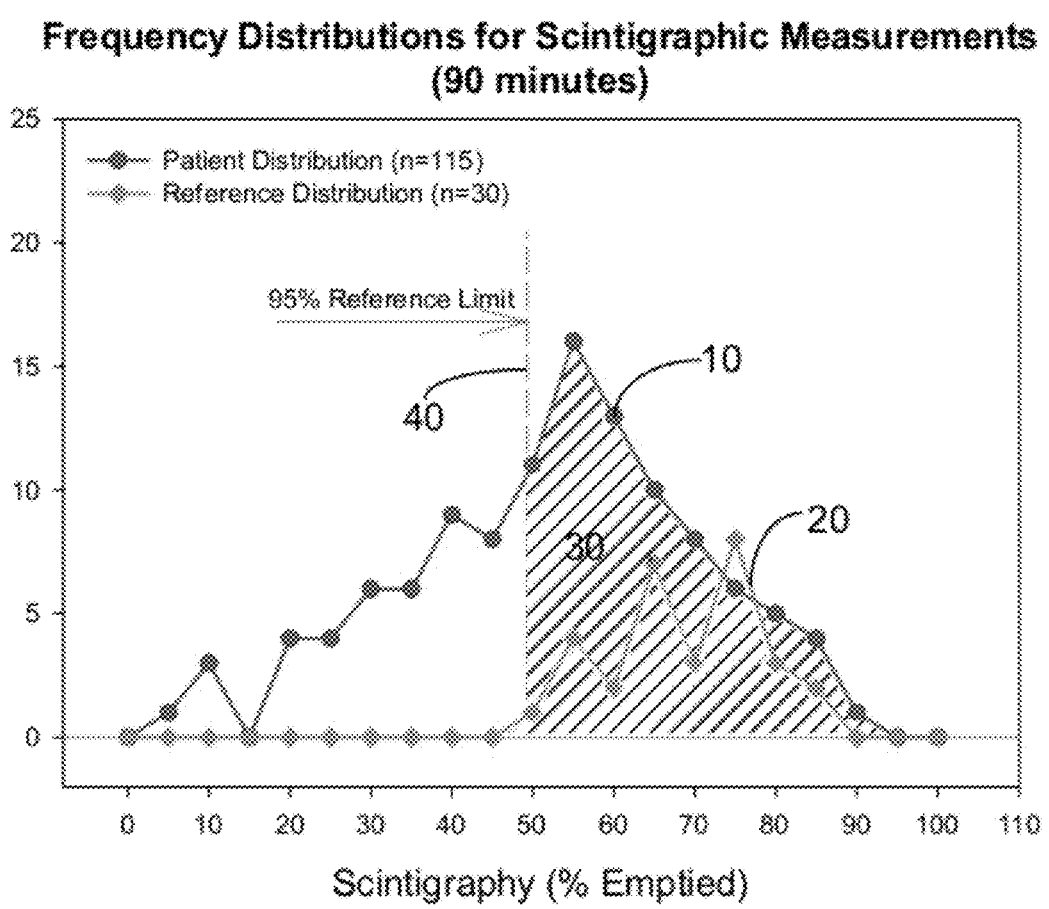
FIG. 1a is a graph showing the unimodal and roughly Gaussian distributions of scintigraphic gastric emptying measurements observed in both healthy patients and patients presenting with symptoms and/or history consistent with delayed gastric emptying.
Figure 1B:
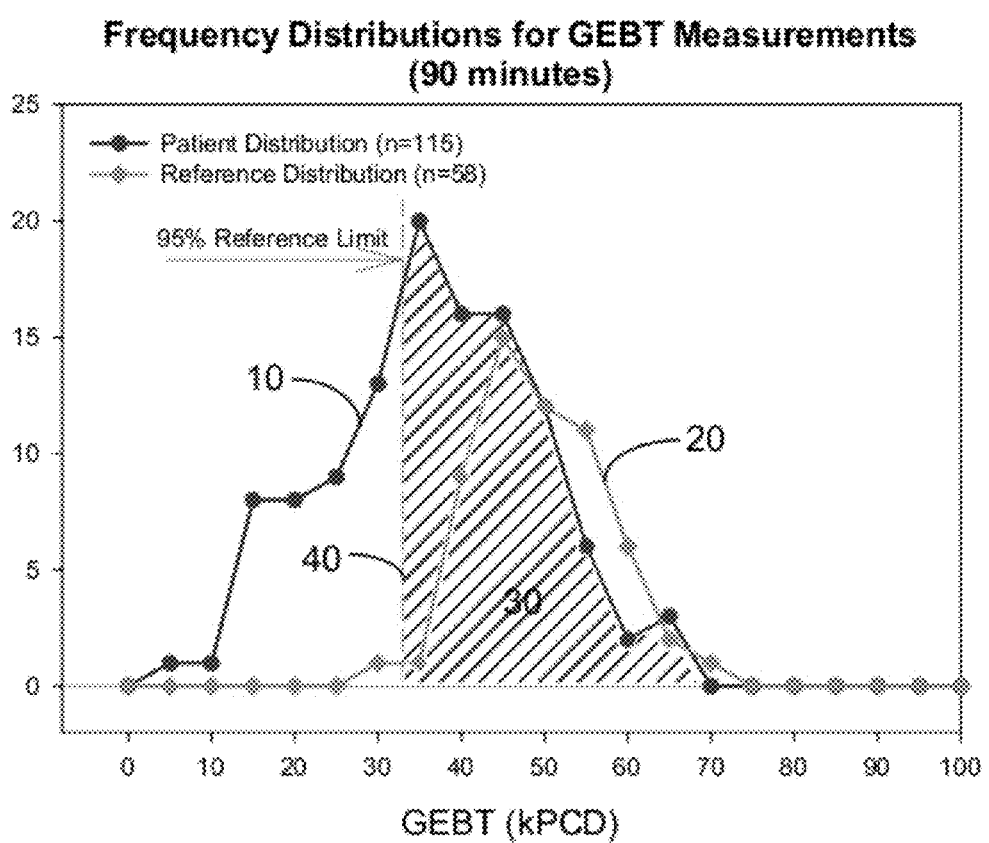
FIG. 1b is a graph showing the unimodal and roughly Gaussian distributions of breath test gastric emptying measurements observed in both healthy patients and patients with symptoms and/or history consistent with delayed gastric emptying.

Examples of the overlap in distributions of gastric emptying rates in patients vs. normal, healthy subjects are shown in both FIGS. 1a and 1b. The Figures demonstrate the gastric emptying rates observed in 115 patients tested for gastroparesis by the method of gastric scintigraphy (in FIG. 1a) and by the method of breath testing (in FIG. 1b) as compared to the rates of gastric emptying observed in a set of healthy, normal ("reference") individuals. The rates of gastric emptying across all 115 patients range from virtually 0 to rates of emptying observed in normal, healthy (reference) individuals. Line 10 represents the distribution of gastric emptying rates for the 115 patients symptomatic for and clinically suspected of having gastroparesis whereas line 20 represents the distribution of gastric emptying rates observed in a set of normal, healthy (reference) individuals. Note the significant area of overlap as shown by the shaded area 30. Because the distribution of gastric emptying rates in patients is unimodal and near Gaussian in nature, and a significant portion of the distribution overlaps with the distribution of rates observed in the healthy (reference) subjects, a simple dichotomous approach to patient characterization and clinical management is inappropriate for evaluation of delayed gastric emptying and is not consistent with clinical reality.

Moreover, a significant number of the 115 patients had gastric emptying rates at or around a simple dichotomous cutoff point (COP) represented by line 40 in FIGS. 1A and 1B. The COP demarcates normal from slow gastric emptying and was established from measurements acquired in the normal, healthy (reference) patients. This area of the patient distribution is highly populated and, in regards to these patients, makes diagnostic and therapeutic intervention somewhat confusing. For example, the lower limit of normal gastric emptying rates as established by the scintigraphic method at the 90-minute time point is 49.4% emptied, as displayed in FIG. 1a. It is clinically unrealistic to classify a patient with a value of 49.3% as positive and treat, vs. classifying a patient with a value of 49.4% as normal and not treat.

The second issue making interpretation of gastric emptying results particularly difficult is the confounding element of significant, natural, within-subject, time-related biologic variation in gastric motility. In any individual, gastric motility normally varies significantly on a daily basis and throughout the day. Therefore, individual results for gastric emptying tests within the same subject will vary throughout the day and from day to day. This normal biological variation makes interpretation of gastric emptying test results, particularly repetitive testing, more difficult than the interpretation of other sorts of tests which have little or no natural biologic variability.

Rates of gastric emptying observed in patients at or around the dichotomous COP will have significant diagnostic uncertainty due to the influence of this natural, day to day, within-subject biologic variation in gastric emptying physiology. Repeat testing of the same patient whose initial result lies about the COP area may result in a reversal of their prior diagnostic classification (normal vs. slow or vice versa) simply due to biologic variation. The amount of uncertainty can be quantified utilizing prospectively collected measurements of within-subject biologic variation. Once measured, a borderline zone can be uniquely constructed about a dichotomous COP utilizing the degree of observed biologic variation.

Applicant has developed a method for categorizing gastric emptying data that addresses the problem of overlapping distributions in regards to measurements of gastric emptying. Furthermore, applicant has measured the significant within-subject day-to-day biologic variation and uniquely utilized the observed amount of biologic variation to construct a polychotomous zone approach to classifying gastric emptying results. Such a classification system improves diagnostic certainty and provides greater clarity for therapeutic intervention.

Applicant has developed a method for categorizing gastric emptying data that takes such borderline zones into account and is applicable to either the method of scintigraphy or breath testing.

Thus, some embodiments provide a gastric classification system and method of classifying gastric emptying data. The classification system includes diagnostic zones that take into account natural biological variation to make the zones particularly useful for interpreting test results. In some cases, the classification system includes an abnormal zone, a borderline zone, and a normal zone. The abnormal zone can be a rapid emptying zone or a delayed emptying zone. In other cases, the classification system includes a rapid emptying zone, a borderline rapid emptying zone, a normal zone, a borderline delayed emptying zone, and a delayed emptying zone. This polychotomous classification system not only provides a more accurate classification of the patient's motility status that is consistent with clinical reality, but the zones can also be created to appropriately manage test results in light of biological variation. In many cases, the zones are calculated using gastric emptying measurements and biologic variation measurements from healthy patients.

The diagnostic zone classification system also classifies gastric emptying measurements at one or more time points. In some cases, the one or more time points include a 45 minute time point, a 90 minute time point, a 120 minute time point, a 150 minute time point and/or a 180 minute time point, depending on the emptying characteristics of the meal chosen.

The gastric emptying test being classified can be any test known in the art. In some cases, the test is a scintigraphy test and the classification system classifies scintigraphic measurements. Scintigraphy testing can be performed according to methods known in the art. In some cases, the scintigraphic test can be administered by supplying the patient with a meal containing a scintigraphic label. The scintigraphic label can be any such label known in the art, such as $^{99m}$Tc sulphur colloid (technetium). In some cases, $^{99m}$Tc sulphur colloid is provided in the meal at a dose of about 0.5 mCi.

The meal can include any food type suitable for human consumption. The term "meal" is referred to herein as any number of edible food components ingested at a single setting. A single setting can be a designated time point, perhaps a period of less than 30 minutes, 20 minutes, or even 10 minutes. In many cases, a meal can include a main food component as well as any sides and liquids. In certain cases, the meal includes components derived from standardized, freeze-dried or lyophilized components. Suitable freeze-dried components are described in U.S. patent application Ser. No. 10/435,092, the entire contents of which are incorporated herein by reference. In one embodiment, the meal includes components derived from lyophilized eggs. In one particular embodiment, the meal includes lyophilized whole eggs that have been reconstituted and $^{99m}$Tc sulphur colloid added. In certain embodiments, the meal includes eggs with $^{99m}$Tc sulphur colloid, bread, and milk, or eggs with $^{99m}$Tc sulphur colloid, crackers and water. In particular cases, the meal includes two scrambled eggs with $^{99m}$Tc sulphur colloid, a slice of wheat toast, and 8 ounces of skim milk.

An exemplary method of classifying scintigraphy testing and using a scintigraphy zone classification system will now be described. A patient preferably fasts for a period of time, for example at least about eight hours, before the test is administered. In addition, the patient preferably refrains from drinking more than about four fluid ounces of water up to one hour before the test. A patient is given a meal that includes a scintigraphic label.

Once the meal is consumed, a gamma emission camera is positioned over the patient's abdomen (often both a posterior and anterior gamma emission camera is used) in order to record the movement of the meal and scintigraphic label out of the stomach. The camera takes scans of the gamma emission from the scintigraphic label at different time points, perhaps at 45, 90, 120, 150, 180, and 240 minute time points, and the gastric emptying measurement at each time point is determined.

Scintigraphic test measurements can be expressed using any metric known in the art. In some cases, the scintigraphic measurements are expressed as Prop$_t$, which is the proportion of a label emptied from the stomach at a given time t. A region of interest is drawn around the stomach on the anterior and posterior images for each time point. To correct for attenuation, the counts of each are multiplied together and the square root of the product are taken to obtain the geometric mean. In other cases, scintigraphic measurements are expressed as $t_{1/2}$, which is a metric representing the half-emptying time of a meal. Here, gastric emptying is mathematically modeled with a power exponential model, from which the diagnostic result $t_{1/2}$ is calculated.

Once the scintigraphic test measurements for each time point are determined, they are placed into a diagnostic zone. The zone can be selected from the group consisting of an abnormal zone, a borderline zone, and a normal zone. The abnormal zone can be a delayed emptying zone or a rapid emptying zone. In particular cases, the zone is selected from the group consisting of a rapid emptying zone, a borderline rapid emptying zone, a normal zone, a borderline delayed emptying zone, and a delayed emptying zone. Applicant has calculated one particular gastric emptying classification system. This classification system is illustrated in Table 1 and can be used for classifying patients suspected of slow or delayed gastric emptying. The zones in this classification system account for normal biological variation of gastric emptying in healthy subjects, as will further be described below. This exemplary three-zone classification is designed to be used in conjunction with a scintigraphic test that involves administering a standardized 225 kCal meal containing eggs and the radioactive $^{99m}$Tc sulphur colloid label. The classification system also assumes that a normal patient ingests the entire meal within ~10 minutes and, in healthy subjects, the entire meal empties in about 180 minutes (3 hours).

TABLE 1

| Time t | Delayed Emptying Metric = % Emptied | Borderline Delayed Emptying Metric = % Emptied | Normal Metric = % Emptied |
|---|---|---|---|
| 45 Minute | <6.3 | 6.3-29.9 | >29.9 |
| 90 Minute | <36.2 | 36.2-62.6 | >62.6 |
| 120 Minute | <56.1 | 56.1-79.5 | >79.5 |
| 150 Minute | <67.0 | 67.0-87.8 | >87.8 |
| 180 Minute | <79.4 | 79.4-95.6 | >95.6 |

A patient's scintigraphic measurement at each time point is placed into one of three zones. A clinician can observe and classify one or more of the time points. As an example, the classification of a patient's result at the 120 minute (2 hour) time point will now be described. If a patient has emptied <56.1% of the meal at 120 minutes, the patient is considered to have delayed emptying and is gastroparetic. The lower the value the slower the rate of gastric emptying, with 0 being a completely non-functional (no motility) stomach. Likewise, if the patient has emptied >79.5% of the meal at 120 minutes, the gastric emptying rate is considered normal. Finally, if the patient has emptied between 56.1% and 79.5% of the meal at 120 minutes, the gastric emptying rate is considered borderline.

Some cases provide a method of classifying scintigraphic test measurements at a 45 minute time point, a 90 minute time point, a 120 minute time point, a 150 minute time point, and a 180 minute time point. The classifying includes (1) selecting a delayed emptying zone when the scintigraphic test measurement is less than 6.3% emptied, selecting a borderline zone when the scintigraphic test measurement is between 6.3 and 29.9% emptied, and selecting a normal zone when the scintigraphic test measurement is greater than 29.9% emptied at the 45 minute time point, (2) selecting a delayed emptying zone when the scintigraphic test measurement is less than 36.2% emptied, selecting a borderline zone when the scintigraphic test measurement is between 36.2 and 62.6% emptied, and selecting a normal zone when the scintigraphic test measurement is greater than 62.6% emptied at the 90 minute time point, (3) selecting a delayed emptying zone when the scintigraphic test measurement is less than 56.1% emptied, selecting a borderline zone when the scintigraphic test measurement is between 56.1 and 79.5% emptied, and selecting a normal zone when the scintigraphic test measurement is greater than 79.5% emptied at the 120 minute time point, (4) selecting a delayed emptying zone when the scintigraphic test measurement is less than 67.0% emptied, selecting a borderline zone when the scintigraphic test measurement is between 67.0 and 87.8% emptied, and selecting a normal zone when the scintigraphic test measurement is greater than 87.8% emptied at the 150 minute time point, or (5) selecting a delayed emptying zone when the scintigraphic test measurement is less than 79.4% emptied, selecting a borderline zone when the scintigraphic test measurement is between 79.4 and 95.6% emptied, and selecting a normal zone when the scintigraphic test measurement is greater than 95.6% emptied at the 180 minute time point.

In some cases, the patient's result is not only placed into one of three zones, the result is also classified within the zone. Each zone can have an intra-zone classification system such as a low intra-zone, a middle intra-zone, and a high intra-zone. For example, if the result is placed into the delayed emptying zone, the result can then be indicated as being in a low-intra zone (closer to a non-functional stomach), being in a high intra-zone (closer to the borderline zone), or being in a middle intra-zone. For example, a result of 55% at the 120 minute time point is first placed within the delayed emptying zone and is then placed in a high intra-zone. Likewise, a result of 57% at the 120 minute time point is first placed within the borderline zone and is then placed in a low intra-zone. Also, a result of 67% is first placed within the borderline zone and is then placed within a middle intra-zone. Finally, a result of 81% is first placed with the normal zone and then is placed in a low intra-zone (or simply placed in the normal zone).

The reference ranges illustrated in Table 1 can be adjusted and changed, such as when new meals of different compositions are developed. Skilled artisans will understand how the reference ranges (and borderline zones) are obtained and can recreate them with new data. In addition, other mechanisms for classifying measurements for breath test and scintigraphic tests (such as the t½ metric) can be used, in order to classify patients into a normal, borderline, or abnormal result.

Figures 2A, 2B, 2C:
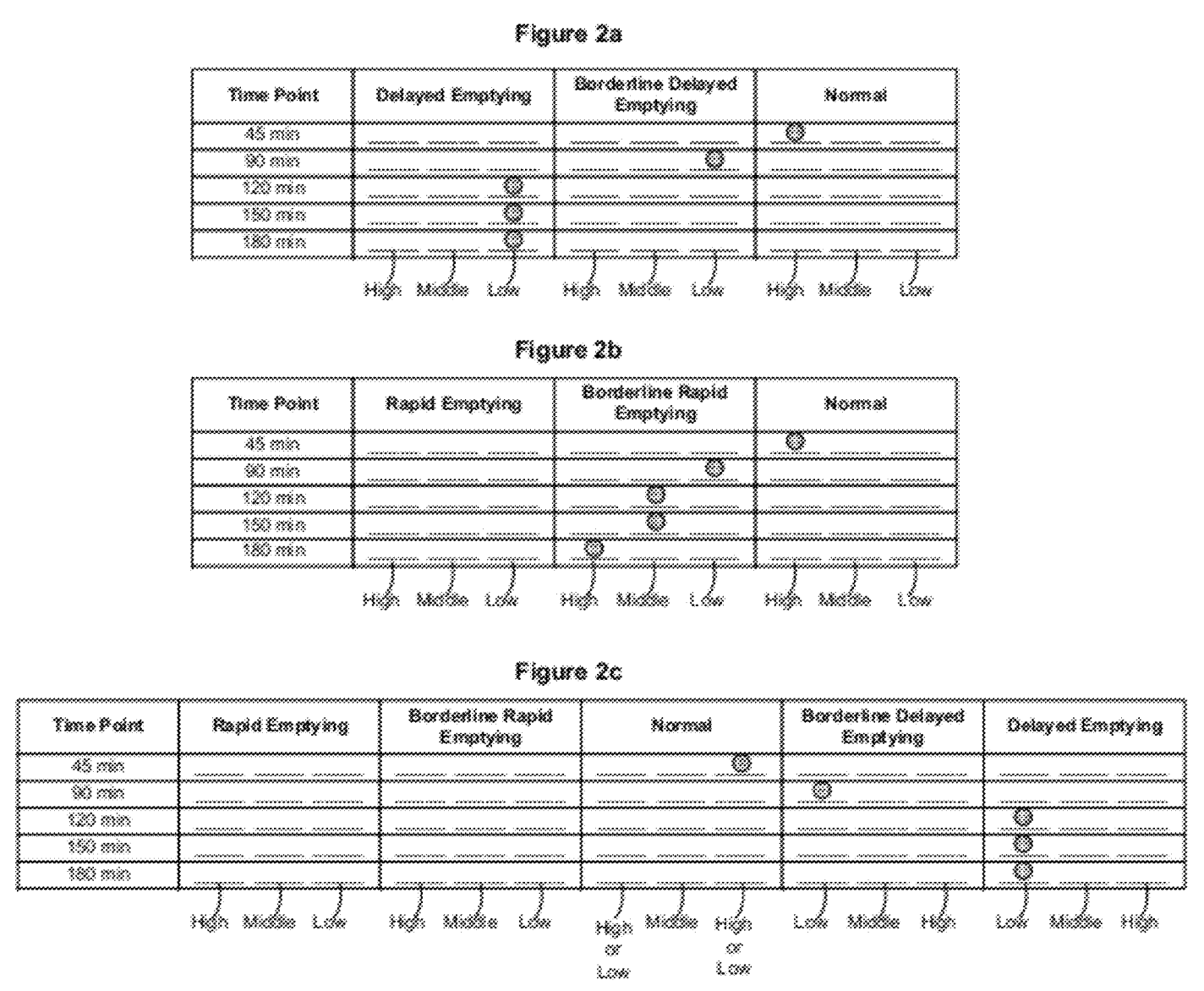

Once the zones (and perhaps the intra-zone classifications) for all of the time points have been determined, the classification can be expressed in a useful format. In some embodiments, the resulting classification can be displayed in an easy to read display, such as in one of the exemplary displays shown in FIGS. 2a-2c. FIG. 2a is a display showing abnormal (delayed) emptying, borderline delayed emptying, and normal categories. FIG. 2b is a display showing abnormal (rapid) emptying, borderline rapid emptying, and normal categories. FIG. 2c is a display showing rapid emptying, borderline rapid emptying, normal, borderline delayed emptying, and delayed emptying categories. The display can be provided in a computerized format for viewing on a computer screen, and/or as a result printout. The display can also be used for data obtained for any type of gastric emptying test, such as a breath test or a scintigraphy test.

As shown in FIGS. 2a-2c, for each time point, the patient's results are both within a zone and also within an intra-zone. Essentially, each classification can provide a range within which the patient's result may be displayed, such that the result does not merely fall within a particular zone, but may be displayed anywhere on a range within that zone. For example, for the borderline delayed emptying, the result may be displayed as being closer to gastroparetic or closer to normal or in between. For normal results, the display may indicate that the result is anywhere from closer to borderline delayed emptying or in between borderline delayed emptying and borderline rapid emptying, or closer to borderline rapid emptying. In the illustrated displays, three intra-zones are provided within each zone. The three intra-zones include a low intra-zone, a middle intra-zone, and a high intra-zone. However, a skilled artisan will understand that any number of intra-zones can be used, such as two, three, or five, intra-zones.

In other cases, the gastric emptying test being classified is a gastric emptying breath test ("GEBT"), and testing can be performed according to methods known in the art. In some cases, the GEBT is administered by supplying the patient with a meal containing a $^{13}$C label. The $^{13}$C label can be provided from any source that is suitable for human consumption. For example, the source can be octanoic acid incorporating $^{13}C$ or even algae labeled with $^{13}C$, such as *Spirulina platensis*, a blue green algae, grown in a highly enriched $^{13}C$ environment. A breath test using *Spirulina platensis* labeled with $^{13}C$ is herein referred to as "$^{13}C$-SpGEBT". Algae containing $^{13}C$ may be obtained by growing the algal cells in a $^{13}C$-enriched environment as is disclosed in commonly assigned U.S. Pat. No. 6,872,516, the disclosure of which is herein incorporated by reference in its entirety. *Spirulina platensis* was acknowledged by the US Food and Drug Administration as a legally marketed food in 1981 and is currently consumed in the US as a dietary supplement. *Spirulina platensis* can be uniformly labeled with $^{13}C$ to an abundance level of approximately 99% and containing 50-60% protein, 30% starch and 10% lipid. $^{13}C$-*Spirulina platensis* can also be provided at a dose of 200 mg or less. In certain cases, the dose is approximately 100 mg, which contains approximately 43 mg of $^{13}C$.

The principle of the $^{13}C$-labeled breath test for assessing gastric emptying and, subsequently, assessing digestive health, takes advantage of the process of food digestion and metabolism which results in the formation of $CO_2$. There are two predominate forms of non-radioactive carbon in nature, our bodies, and the food we eat. Carbon-12, denoted as $^{12}C$, occurs in a natural abundance of approximately 99%. Carbon-13, denoted as $^{13}C$, occurs in a natural abundance of approximately 1%. A third type (isotope) of carbon is radioactive Carbon-14, but its natural abundance is minute and it is not used in stable isotope breath testing. If a breath test substrate is "reverse labeled," so that it is rich in $^{13}C$ instead of $^{12}C$, then the increased signal from the introduction of non-endogenous $^{13}C$ to the patient can be detected in the breath after the substrate has undergone digestion, absorption and metabolism. The digestive and metabolic processes give rise to $CO_2$ as an end product. Hence, as the $^{13}C$ labeled meal is triturated by the stomach it passes through the pylorus into the intestines where the components of the $^{13}C$-labeled substrate, such as a substrate like *Spirulina* biomass, are digested, absorbed, and metabolized, giving rise to $^{13}CO_2$ expired in the breath. Breath samples, collected before and after the test meal at strategic time points, are analyzed to determine the ratio of $^{13}CO_2/^{12}CO_2$ in each breath sample. This ratio is then used to calculate the change in $^{13}CO_2$ excretion over time. By measuring the change in $^{13}CO_2$ excretion over time, the rate of gastric emptying can be determined.

The breath test meal can include any food type suitable for human consumption and can be of the type described above with respect to scintigraphic testing. In one particular embodiment, the meal includes whole eggs and $^{13}C$-*Spirulina platensis* that has been lyophilized together and then reconstituted. For example, a lyophilized powder containing both a pasteurized scrambled egg mix and approximately 100 mg of $^{13}C$-*Spirulina platensis* is rehydrated with potable water. The egg mix is then cooked, for example in a microwave. A patient can be administered the cooked egg mix along with other optional edible food components, such as six Nabisco PREMIUM Saltine crackers and six ounces of potable water.

One exemplary method of classifying a breath test and using a breath test classification system will now be described. A patient preferably fasts for a period of time, for example at least about eight hours, before the tests are administered. In addition, the patient preferably refrains from drinking more than about four fluid ounces of water up to one hour before the test. A baseline breath sample is collected before the meal is administered to determine the initial ratio of $^{13}CO_2/^{12}CO_2$ in the baseline (pre-meal) breath. A patient is then given a meal that includes >95% $^{13}C$-labeled *Spirulina platensis*. The patient also consumes the meal in a single setting, preferably within a 10 minute time frame.

After the meal is consumed, breath samples are obtained after the meal is consumed at periodic time points, such as at 45, 90, 120, 150, 180, and 240 minute time points. In some cases, breath samples are collected in glass tubes using a straw to blow into the bottom of the tube to displace contained air. The tubes are capped and the $^{13}CO_2$ content of the breath for each tube (and thus for each time point) is determined using Gas Isotope Ratio Mass Spectrometry and/or Infrared Spectroscopy. For example, gas isotope ratio mass spectrometers (manufactured by Europa Scientific, UK) and infrared spectrometers (available from Otuska Electronics Co., Ltd.) have been approved by the FDA for measurements of $^{13}CO_2/^{12}CO_2$ ratios in human breath. Breath samples, collected before and after the test meal, are analyzed to determine the ratio of $^{13}CO_2/^{12}CO_2$ in the sample. This ratio is then used to calculate the change in $^{13}CO_2$ excretion over time and thus provide a breath test measurement.

The breath test measurement can be expressed using any metric known in the art. Applicant has developed two novel metrics in common to express breath test measurements: kPCD and CumPCD. Thus, in certain cases, the breath test measurement is expressed as kPCD and CumPCD. The PCD metric is the Percent Dose (abbreviated PCD) of $^{13}C$ excreted at time t after consumption of the test meal. To provide a more convenient scale, PCD is multiplied by 1000 to produce kPCD at any time, t. CumPCD is the cumulative dose of $^{13}C$ excreted at time t. The kPCD and CumPCD can be determined for each time point t after consumption of the test meal, usually at 45, 90, 120, 150, 180, and 240 minute time points. For each time t, the kPCD can be calculated as follows:

$$kPCD_t = \left[\frac{DOB * CO_2PR * R_s * 13}{10 * dose}\right] * 1000$$

where:

DOB=The measured difference in the $^{13}CO_2/^{12}CO_2$ ratio between a post-meal breath specimen at any time t and the baseline breath specimen.

$CO_2PR$=$CO_2$ production rate (mmol $CO_2$/min) calculated using the Scholfield equations. The Scholfield equations are a set of equations which are fitted to people depending on their age, gender, height, and weight to estimate the basal metabolic rate (BMR), which is intimately related to $^{13}CO_2$ production rate. The equations are known in the art and allow the calculation of a specific $CO_2$ production rate for the individual being tested.

$R_s$=0.0112372, the ratio [$^{13}CO_2/^{12}CO_2$] in an international reference standard (Pee Dee Belemite).

13=The atomic weight of $^{13}C$.

10=A constant factor for converting units.

Dose=The weight (mg) of $^{13}C$ in the dose of $^{13}C$-*Spirulina platensis* administered to the patient in the test meal. For example, since $^{13}C$-*Spirulina platensis* is approximately 43% by weight $^{13}C$, a dose of 100 mg corresponds to approximately 43 mg of $^{13}C$.

The kPCD is calculated for each time point t, which in certain cases includes 45, 90, 120, 150, 180, and 240 time points. Applicant also calculates CumPCD (Cumulative PCD). The CumPCD is the calculation of the area under the PCD curve and is accomplished by trapezoidal integration:

$$CUMPCD_n = \sum_{i=1}^{i=n} \frac{(PCD_i + PCD_{i-1})(t_i - t_{i-1})}{2}$$

where $PCD_i$ and $t_i$ represent the PCD value (in μmol/min) and time (in minutes) at the $i^{th}$ breath collection time point.

Figure 3:
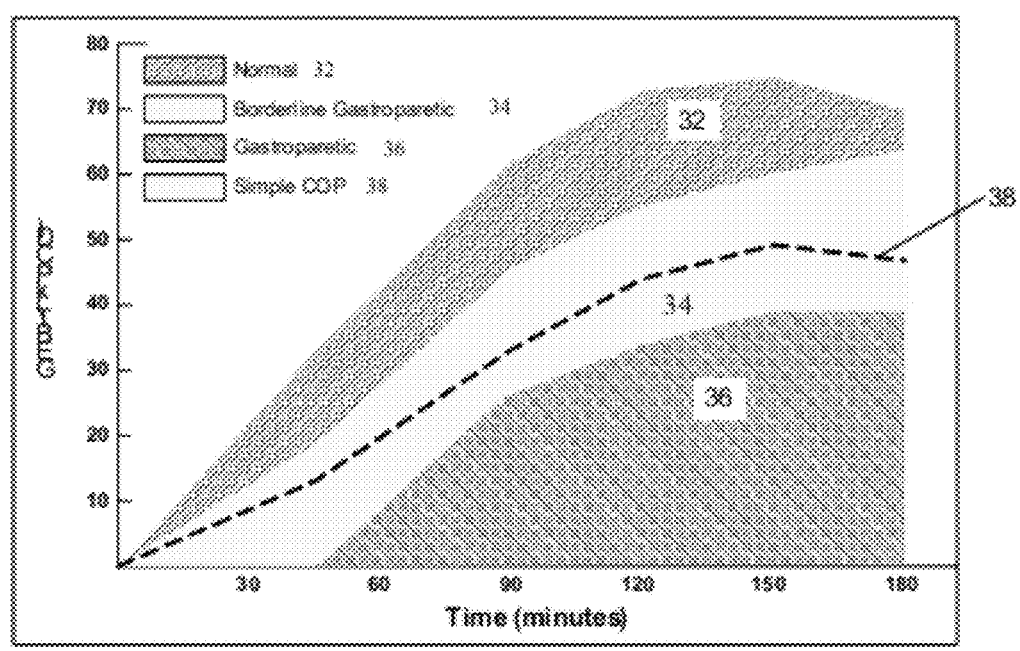
FIG. 3 is a graph of GEBT results over time.

Once the GEBT measurements for each time point is determined, they are placed into a zone. The zone can be selected from the group consisting of an abnormal zone, a borderline zone, and a normal zone. The abnormal zone can be a delayed emptying zone or a rapid emptying zone. In particular cases, the zone is selected from the group consisting of rapid emptying, borderline rapid emptying, normal, borderline delayed emptying, and delayed emptying. Table 2 displays an exemplary three-zone classification scheme for classifying patients suspected of delayed gastric emptying. This exemplary three-zone classification system is designed to be used in conjunction with a breath test that involves administering to a patient a meal containing eggs and $^{13}C$-Spirulina. The classification system also assumes that a normal patient ingests and empties the meal within ~3 hours (180 minutes). This exemplary classification system is also illustrated in FIG. 3, where line 38 is the simple dichotomous cutoff point for demarcating delayed emptying from normal emptying. The shaded area 32 above the line 38 displays the normal zone, the area 36 below the line displays the delayed emptying zone, and the area 34 in between areas 32 and 36 displays the borderline zone.

TABLE 2

| Time t | Delayed Emptying Metric = kPCD | Borderline Delayed Emptying Metric = kPCD | Normal Metric = kPCD |
| --- | --- | --- | --- |
| 45 Minute | <6.3 | 6.3-19.5 | >19.5 |
| 90 Minute | <21.9 | 21.9-44.2 | >44.2 |
| 120 Minute | <33.1 | 33.1-55.3 | >55.3 |
| 150 Minute | <39.5 | 39.5-59.1 | >59.1 |
| 180 Minute | <38.1 | 38.1-54.9 | >54.9 |

The patient's result for one or more time points is placed into one of the three zones. As an example, the classification of the patient's result at the 120 minute (2 hour) time point will now be described. If a patient's kPCD value at 120 minutes is <33.1, that value is placed in the delayed emptying zone and the patient's gastric emptying at the 120 minute time point is considered to be delayed. The lower the value, the slower the rate of gastric emptying, with 0 being a completely non-functional stomach. Likewise, if the patient has a kPCD value >55.3 at 120 minutes, that value is placed within the normal zone and the patient's gastric emptying rate at the 120 minute time point is considered normal. Finally, if the patient has a kPCD value between 33.1 and 55.3 at the 120 minute time point, the gastric emptying rate is considered borderline.

Some cases provide a method of classifying breath test measurements at a 45 minute time point, a 90 minute time point, a 120 minute time point, a 150 minute time point, and a 180 minute time point. The classifying includes: (1) selecting a delayed emptying zone when the breath test measurement is less than 6.3 kPCD, selecting a borderline zone when the breath test measurement is between 6.3 and 19.5 kPCD, and selecting a normal zone when the breath test measurement is greater than 19.5 kPCD at the 45 minute time point, (2) selecting a delayed emptying zone when the breath test measurement is less than 21.9 kPCD, selecting a borderline zone when the breath test measurement is between 21.9 and 44.2 kPCD, and selecting a normal zone when the breath test measurement is greater than 44.2 kPCD at the 90 minute time point, (3) selecting a delayed emptying zone when the breath test measurement is less than 33.1 kPCD, selecting a borderline zone when the breath test measurement is between 33.1 and 55.3 kPCD, and selecting a normal zone when the breath test measurement is greater than 55.3 kPCD at the 120 minute time point, (4) selecting a delayed emptying zone when the breath test measurement is less than 39.5 kPCD, selecting a borderline zone when the breath test measurement is between 39.5 and 59.1 kPCD, and selecting a normal zone when the breath test measurement is greater than 59.1 kPCD at the 150 minute time point, or (5) selecting a delayed emptying zone when the breath test measurement is less than 38.1 kPCD, selecting a borderline zone when the breath test measurement is between 38.1 and 54.9 kPCD, and selecting a normal zone when the breath test measurement is greater than 54.9 kPCD at the 180 minute time point.

Like scintigraphy, the patient's breath test measurement can not only be placed into one of three zones, but can also be classified within the zone. Each zone can have an intra-zone classification system, such as a low intra-zone, a middle intra-zone, and a high intra-zone. For example, a measurement of 32 kPCD at the 120 minute time point is first placed within the delayed emptying zone and is also placed within a low intra-zone (indicating that it is closer to the borderline zone). Likewise, a measurement of 34 kPCD at the same time point is first placed within the borderline zone and is also placed within a high intra-zone (indicating that it is closer to the delayed emptying zone). Also, a measurement of 54 kPCD is first placed within the borderline zone and is also placed within a low intra-zone (indicating that it is closer to the normal zone). Finally, a measurement of 56 kPCD is first placed within the normal zone and is also placed within a high intra-zone (indicating that it is closer to the borderline zone).

Figure 4:
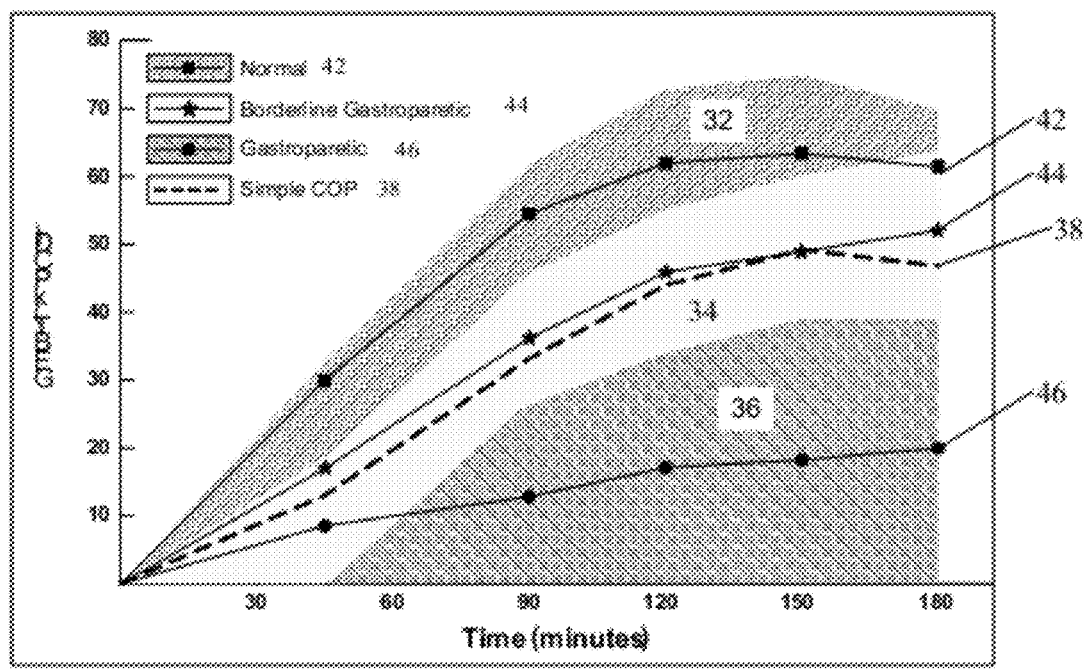
FIG. 4 is a graph of GEBT results over time, which illustrates gastric emptying measurements for three patients.

Diagnostic zone classifications for GEBT results can also be provided in any desired format. In certain embodiments, the GEBT results are expressed using an easy to read display, as already described with respect to FIGS. 2a-2c. In other cases, the results can be displayed in the form of a graph, perhaps as a graph as illustrated in FIG. 4. FIG. 4 shows the same zone classification scheme as FIG. 3, but further includes results for three patients. Line 42 represents results for a normal patient, line 44 represents results for a borderline delayed emptying patient, and line 46 represents results for a delayed emptying patient.

Once the patient's classification scheme is displayed, a clinician can use this display to not only diagnose the patient but assess the patient's stomach emptying rate and observe any trends over time. Such observations may be useful in correlating the patient's gastric emptying pattern with an appropriate treatment plan which corresponds to the pattern. In addition, by displaying a range of results within each of the categories, as done with the displays of FIGS. 2a-2c, the physician can assess the likelihood of an abnormality or assess the severity of the abnormality in more detail than simply identifying a classification. The display can also be used for comparing the results of tests performed at different times, such as for example, when the test is repeated in the future. Such future tests may be performed after the introduction of a treatment plan or after a change in the treatment plan, and changes to gastric emptying can be more easily evaluated by comparing the display of the results for each test. Such a comparison using the display allows the clinician to evaluate the effectiveness of a treatment at each time point of the test. Not only can the clinician check for whether a patient's classification improved (e.g., from delayed emptying to borderline delayed emptying) at each time point of the test, but the clinician can also check for improvement from within a classification (e.g., a shift from very highly or severely delayed emptying to delayed emptying that is closer to borderline).

Furthermore, when gastric emptying data is classified according to zones, degrees of therapeutic action may be more appropriately applied. In this way, the selected treatment can more precisely correlate with a patient's gastric emptying pattern. Thus, in some embodiments, a method of treating a patient can be provided. The method can include performing a gastric emptying test on a patient, obtaining a gastric emptying measurement at a desired time point (e.g., the 90, 120 or the 180 minute time point), and classifying the gastric emptying measurement at that time point. The classifying can include placing the gastric emptying measurement into one or more zones selected from the group consisting of an abnormal zone, a borderline zone, and a normal zone, wherein the abnormal zone is either a delayed emptying zone or a rapid emptying zone and wherein the borderline zone is either a delayed emptying borderline zone or a rapid emptying borderline zone.

In some cases, the zone is selected from the group consisting of rapid emptying, borderline rapid emptying, and normal. In other cases, the zone is selected from the group consisting of delayed emptying, borderline delayed emptying, and normal. In yet other cases, the zone is selected from the group consisting of rapid emptying, borderline rapid emptying, normal, borderline delayed emptying, and delayed emptying. The method also includes selecting a level of therapeutic action based on the selected zone. In many cases, the action is selected with a goal of restoring hydration and nutrition to a patient while also trying to relieve symptoms, which may include satiety, nausea, vomiting, bloating and upper abdominal discomfort.

The selected treatment or therapeutic action can be none for normal patients, a delayed emptying mild action or a delayed emptying modest action for borderline delayed emptying patients, and a delayed emptying aggressive action or a delayed emptying very aggressive action for delayed emptying patients. Likewise, the selected treatment can be none for normal patients, a rapid emptying mild action or modest action for borderline rapid emptying patients and a rapid emptying aggressive action or a rapid emptying very aggressive action for rapid emptying patients or borderline patients who do not respond to lesser therapies. Thus, the severity of delayed or rapid emptying can serve as a guide that drives increasingly aggressive therapy. If the mild action does not appear to be alleviating symptoms in a borderline patient, an aggressive action can subsequently be applied.

Delayed emptying mild actions can include adjusting a patient's diet and/or requesting a patient to engage in exercise. In some cases, the patient is asked to refrain from eating meals high in fat and insoluable fiber, as these retard gastric emptying. Instead, the patient can eat numerous small, low fat meals consisting of complex carbohydrates. The delayed emptying mild action can also include restoring glycemic control in diabetic patients.

Where delayed emptying mild actions do not work, or when a patient is categorized as having delayed emptying beyond the borderline zone, delayed emptying aggressive actions can be taken. Delayed emptying aggressive actions can include administering pharmaceutical agents such as prokinetic agents for increasing gastric motility and/or antiemetic drugs for treating nausea and vomiting. Some borderline patients failing mild therapy may benefit too from a short term or low dose pharmaceutical agent. Hence, the initial dose of pharmaceutical agents can also be correlated to the zone classification and/or symptom severity.

When delayed emptying aggressive therapies do not work, or when a patient is categorized as having severe delayed emptying and/or their nutritional health is significantly at risk, very aggressive delayed emptying actions may be taken. Delayed emptying very aggressive actions can include invasive procedures or surgical procedures, such as venting or feeding ostomies, implantation of gastric pacemakers, and other surgeries. For example, in some severe gastroparetics, particularly diabetics, prolonged periods of increased pyloric tone and contraction have been demonstrated, which may be giving rise to extended gastric retention. These patients can be treated by endoscopically delivering an intrapyloric injection of botulinum toxin, the purpose of which is to relax the pyloric valve, improve gastric emptying and relieve symptoms. In difficult refractory patients with severe nausea and vomiting, a gastrostomy tube can be used to decompress the stomach by venting or suction. Venting jejunostomy may also be employed for symptom relief and to provide parenteral nutrition to these patients. Gastroparetics showing little functional gastric motility can receive surgically placed gastric pacemakers.

Rapid emptying mild actions can include adjusting a patient's diet in order to slow down the rate of gastric emptying. For example, the patient can be instructed to eat small meals that contain increased levels of protein, fiber, pectin and low levels of simple carbohydrates. Also, liquids can be minimized with meals. The patient can also be requested to make changes in posture, such as lying down after a meal, in order to slow down the rate of gastric emptying.

When rapid emptying mild actions do not work, or in patients categorized as having rapid emptying beyond of the borderline zone, a rapid emptying aggressive action can be taken. Rapid emptying aggressive actions can include administering pharmaceutical agents to a patient. Pharmaceutical agents that can be used include drugs that slow down gastric and intestinal motility, such as acarbose (delays digestion of carbohydrates) and octreotide (an antidiarrheal that slows down intestinal motility).

When rapid emptying aggressive actions do not work, or in patients categorized as having severe rapid emptying, a rapid emptying very aggressive action can be taken. Rapid emptying very aggressive actions can include surgical procedures such as pylorus reconstruction or reversal of gastric bypass surgery.

The method of treating a patient can also include measuring the normal day to degree of within-subject biological variation in the rate of gastric emptying and using the observed biological variation to calculate a therapeutic critical increase or critical decrease value. Examples for calculating normal, within-subject day to day biologic variation in gastric emptying and subsequently calculating a critical increase or critical decrease value are described in more detail below. The critical increase indicates how much a gastric emptying measurement must increase in order to reflect a true change in the patient's result in the presence of random, normal, within-subject biologic variation. Likewise, the critical decrease indicates how much a gastric emptying measurement must decrease to reflect a true change in the patient's result. The type or degree of therapeutic action selected can also be determined based on how large or small the critical increase or decrease is. Once treatment is administered, a clinician can then perform an additional gastric emptying test on the patient to determine if the critical increase or critical decrease value has been reached.

Some embodiments also provide methods for developing a zone classification system. Various methods may be used for determining the upper and lower limits of each zone. In some embodiments, the method of developing a zone classification system includes calculating the upper and lower values of each zone using the amount of normal biologic variation associated with gastric emptying. The method can include (1) performing gastric emptying tests on a series of healthy patients, (2) obtaining gastric emptying measurements for the series of healthy patients at a desired time point, (3) using the gastric emptying measurements to form a reference interval for the desired time point, (4) using an upper fractile or a lower fractile of the reference interval as a cutoff point for demarcating normal gastric emptying measurements from abnormal gastric emptying measurements, (5) measuring the within-subject biological variation of gastric emptying rates for a series of healthy patients and modestly impaired patients at the desired time point to obtain biologic variation measurements, and (6) calculating a normal zone, a borderline zone, and an abnormal zone, the borderline zone being calculated around the cutoff point using the degree of biologic variation observed from the biologic variation measurements. The reference interval used can be a 95% reference interval or a lesser interval such as a 90% reference interval or a 85% reference interval. Also, in some cases, the upper fractile is an upper 2.5% fractile and the lower fractile is a lower 2.5% fractile. The upper fractile can be used as an upper cutoff point to demarcate normal gastric emptying measurements from rapid gastric emptying measurements. Likewise, the lower fractile can be used as a lower cutoff point to demarcate normal gastric emptying measurements from delayed gastric emptying measurements.

In certain embodiments, the method includes the following 5 steps: (1) collecting gastric emptying values in healthy subjects for each chosen time point t (using any known method); (2) using the gastric emptying values to construct a 95% reference interval for each time point t, (3) using the lower 2.5% fractile of the 95% reference interval as the simple dichotomous cutoff point for demarcating normal gastric empting values from slow gastric emptying values (or using the upper 2.5% fractile of the 95% reference interval as the simple dichotomous cutoff point for demarcating normal gastric empting values from rapid gastric emptying values); (4) measuring the natural day to day normal biologic variation of gastric emptying in healthy subjects and modestly impaired subjects, and (5) calculating a borderline delayed emptying zone (or a borderline rapid emptying zone) around the simple dichotomous cutoff point using natural day to day biologic variation measurements.

An exemplary method for developing a three-zone classification system, including delayed emptying, borderline delayed emptying, and normal zones will now be described, in accordance with certain embodiments. Skilled artisans will understand that these methods can also be used for developing a rapid emptying, borderline rapid emptying, and normal zones.

Applicant performed the above steps to develop a three-zone classification system for each breath testing and scintigraphy. First, Applicant performed a $^{13}$C-$Spirulina$ Gastric Emptying Breath Test on 65 healthy subjects utilizing a standardized 225 kCal meal that includes potable water, six Nabisco PREMIUM crackers and lyophilized whole eggs-$^{13}$C-$Spirulina$ $platensis$. Likewise, Applicant separately performed scintigraphy testing on 30 healthy subjects using the same standardized meal, but instead includes lyophilized whole eggs with $^{99m}$Tc sulphur colloid added. The healthy subjects passed a physical exam conducted by a physician and were subjected to lab testing, in order to be considered "healthy". Gastric emptying values were obtained at 45, 90, 120, 150, and 180 minute time points.

Second, for each method, Applicant used the gastric emptying values to construct a 95% reference interval for each time point. The 95% reference interval was calculated on both sets of data using RefVal, a program implementing the recommendations of the International Federation of Clinical Chemistry on the statistical treatment of reference values. Though several statistical procedures may be implemented in RefVal, Applicant used the parametric estimation method based on a two-stage mathematical transformation of data: (1) Manly's exponential transformation (to remove skewness) and (2) John and Draper's modulus transformation (to adjust for residual kurtosis). The 95% reference intervals resulting from these calculations are displayed in Table 3.

TABLE 3

95% Central Reference Intervals for the Breath Test and Scintigraphy

| Measurement Time (minutes) | Breath Test (kPCD) | Scintigraphy (Prop) |
|---|---|---|
| 45 | 12.9-32.9 | 18.1-50.5 |
| 90 | 33.1-63.2 | 49.4-80.9 |
| 120 | 44.2-72.5 | 67.8-95.1 |
| 150 | 49.3-74.5 | 77.4-100 |
| 180 | 46.5-70.5 | 87.5-100 |

Third, for each time point, Applicant established a cutoff point ("COP") that distinguishes between normal and delayed emptying. In certain cases, the COP is defined as the 0.025 fractile (2.5%) bound of the central 0.95 (95%) reference range of the metric defined for each method. In the present example, Applicant used the lower limit of each of the 95% reference ranges for each time t displayed in Table 3. In Table 3, the COP for time point 45 minutes is 12.9 kPCD for breath testing and 18.1 Prop for scintigraphy testing. The COP for time point 90 minutes is 33.1 kPCD for breath testing and 49.4 Prop for scintigraphy testing, and so on. If Applicant were instead establishing a classification system for rapid emptying, rapid emptying borderline, and normal, the upper 2.5% COP would be used as the COP that distinguishes between normal and rapid emptying. For example, the upper COP for time point 45 minutes is 32.9 kPCD for breath testing and 50.5 Prop for scintigraphy testing, and so on.

Fourth, after determining the COP for each time point, Applicant measured the amount of within-subject, day to day natural biologic variation with respect to each time point. This biologic variation amount can be measured using known methods in the art. To calculate natural, day to day, within-subject biologic variation, Applicant studied 73 subjects by breath test (65 healthy and 8 marginally gastroparetic) and 28 subjects (20 healthy and 8 marginally gastroparetic) by scintigraphy. Applicant measured the biologic variation by administering to subjects the same gastric emptying test (e.g., the same meal with the same marker in the same dosage) on two independent days (i.e., a first day and a second day). From this data the pooled within subject standard deviation (SD) and the % coefficient of variation (% CV) was calculated. Applicant observed that the degree of variability found in healthy subjects was not statistically different from that found in modestly impaired subjects whose rates of gastric emptying reside in the borderline zone. Applicant obtained the exemplary set of biological variation values that are illustrated in Table 4 below.

TABLE 4

| Procedure | df | Time Points | | | | | |
|---|---|---|---|---|---|---|---|
| | | 45 MIn | 90 Min | 120 Min | 150 Min | 180 Min | 240 Min |
| Breath Test $(SD)_{BV}$ | 73 | 4.0 | 6.8 | 6.8 | 5.9 | 5.1 | 4.4 |
| Breath Test $(\% CV)_{BV}$ | | 17.5 | 14.1 | 11.6 | 9.6 | 8.8 | — |
| Scintigraphy $(SD)_{BV}$ | 28 | 7.2 | 8.0 | 7.1 | 6.3 | 4.9 | 3.3 |
| Scintigraphy $(\% CV)_{BV}$ | | 21.0 | 12.3 | 8.7 | 7.1 | 5.2 | — |

*GEBT results are in kPCD and Scintigraphy results are in percent emptied.
**Note that the data at 240 minutes in not calculable in some cases because the 225 kCal standardized meal used in the study is virtually 100% emptied in ~180 minutes.

Fifth, Applicant used the amount of biologic variation observed (SD) to mathematically construct a borderline zone around the established COP. Because of normal day to day biologic variation, the classification of a patient as delayed or normal could change upon repeat analysis for those patients with values close to the simple COP. A classification system is provided that accounts for potential intra-patient biologic variation. Patient results outside the borderline zone have a very high probability (>95%) of remaining correctly classified, e.g., as delayed or normal, even upon repeat analysis. For example, data regarding normal, within-subject, biologic variation can be used to calculate the borderline zone using the following equation:

BV Borderline zone=Simple COP+/-1.645*$SD_{BV}$ where BV is Biological Variation. The constant 1.645 in the above equation represents a diagnostic efficiency level set at the 95% level. The result is an area (zone) around the COP whose limits are equal to a distance of 1.645*$SD_{BV}$ above and below the simple COP. Hence, The borderline zone will have a first COP and a second COP, with the first COP being an upper limit of the borderline zone, $BV_{upper}$, and the second COP being a lower limit of the borderline zone, $BV_{lower}$. Test results that are above the upper limit of the borderline zone, $BV_{upper}$, are placed into a normal zone and those below the lower limit of the borderline zone, $BV_{lower}$, are placed into a delayed emptying zone. Test result values above the $BV_{upper}$ and below the $BV_{lower}$ COP's have >a 95% probability of being classified properly as normal or delayed, even upon repeat testing. The result is a three zone or trichotomous patient classification system which more accurately characterizes patient gastric motility status.

Applicant chose the 95% level of diagnostic efficiency in the above example in order to achieve a highly confident classification procedure. However, the diagnostic efficiency level chosen could be set lower at the 90%, 85% or 80% level.

The BV Borderline zone using the 95% diagnostic efficiency level can be calculated using the following procedure. Applicant first calculated the 95% reference interval on the 65 healthy patients described previously. Applicant also calculated the pooled, time related, within subject variability (biologic variability) in the subjects and study described previously. The values are used in the following derivation of the borderline zone.

Definitions:
$\mu_i$=the true value of Gastric Emptying in the $i^{th}$ patient
$x_i$=the measured value of Gastric Emptying in the $i^{th}$ patient
$x_o$=the estimated limit of normal results
The $\mu_i$ is the true gastric emptying rate of the patient (for example, it can be found, or at least approached, by measuring the patient's gastric emptying rate the same way, with an error free method, 1,000 times). The $x_i$ is the actual result as measured by the test method. The $x_o$ is the value of the single COP for use in the absence of biologic variation, that is, the simple lower 95% dichotomous COP of the reference interval. For example, the $x_o$ can be taken from Table 3, where it is 12.9 at 45 minutes, 33.1 at 90 minutes, 44.2 at 120 minutes, 49.3 at 150 minutes and 46.5 at 180 minutes. For a given patient, Sensitivity and Specificity are defined as follows (when, as in our case, abnormals have lower values than normals):

Sensitivity=Prob($x_i$,$x_o$|$\mu_i$≤$x_o$)

(the vertical bar in the probability statement means given that.)

Specificity=Prob($x_i$>$x_o$|$\mu_i$>$x_o$)

Then the Diagnostic Efficiency (average value of Sensitivity and Specificity), in the absence of error in the estimated lower limit of normals ($x_o$), is calculated as follows:

$$DiagnosticEfficiency = \int_{-\infty}^{z_{oi}} \Phi(z)\,dz$$

where
$\Phi(z)$=the standard Normal (Gaussian) distribution $$z_{oi} = \frac{[|\mu_i - x_o|]}{\sigma_{ABi}} \quad \text{Eq (1)}$$

$\sigma_{ABi}$=a standard deviation that combines analytical and within-patient, time-related biologic variability.

A rearrangement of Eq (1) can be used to estimate the cutoff limits of the 'borderline' zone for a given diagnostic efficiency.

$COP_1=x_0+z_{oi}\cdot\sigma_{ABi}$ $COP_2=x_0-z_{oi}\cdot\sigma_{ABi}$

As an example, for the GEBT with a lower limit of the reference range for normals, $x_0$, that is determined to be 50.0 and $\sigma_{ABi}$=5.0, to achieve a diagnostic efficiency of 95%, one sets $z_{oi}$=1.645 and solves for $COP_1$ and $COP_2$. In this case, the cutoff points ($COP_1$ and $COP_2$) for the borderline zone become 50.0±8.2, or 58.2 and 41.8, respectively. Thus, a patient with a kPCD>58.2 would be classified as normal. A patient with a kPCD<41.8 would be classified as having delayed gastric emptying and a patient with a value between 41.8 and 58.2 would be classified as being borderline gastroparetic.

In some embodiments of the invention, once the borderline zone is determined, for delayed emptying, negative or normal results can be taken as all values greater than the upper limit of the borderline zone. Positive values can be taken as all values less than the lower limit of the borderline zone. Values between the upper and lower limits of the borderline zone are classified as borderline. The result is a three zone or trichotomous patient classification system which more accurately characterizes patient conditions involving dysmotility of the stomach. These zones are beneficial because gastric emptying has relatively high within-subject, time-related biologic imprecision which can lead to diagnostic misclassifications during routine testing.

In addition to the ability to establish diagnostic zones of high clinical utility, measurements of normal biologic variability have an additional role. The measurements of normal biologic variability can assist a physician in monitoring a patient's therapy. If the degree of normal biologic variability is not known, then the degree to which a therapeutic action can be deemed successful will be unknown or will be mistakenly understood. However, when the degree is known, it can be used to inform the physician regarding how much the rate of gastric emptying must change in order that the rate change not to be due to simple normal, random biologic variation. In certain embodiments, the degree of biologic variation can be used to calculate a critical increase ($\Delta_\uparrow$) or a critical decrease ($\Delta_\downarrow$) value, which indicates how much a gastric emptying value must increase or decrease in order to reflect a true change in the patient's result from therapy and not random biologic variation. The $\Delta_\uparrow$ or $\Delta_\downarrow$ can be calculated using standard statistical equations, provided the degree of biologic variation is known.

In one embodiment, the critical increase, $\Delta_\uparrow$, may be determined as follows. The $\Delta_\uparrow$ in kPCD (for breath testing) or in % Emptied (for scintigraphy) that is more than 95% likely to indicate a true change in the patient result (i.e., is <5% likely to be attributable to random variation ($S_{tot}$)) is given by:

$$\Delta_\uparrow = \sqrt{2} \times z_{1-\alpha} \times S_{TOT} + 1.35 \times RIS$$

where, $z_{1-\alpha}$=the standard normal variable corresponding to probability (1−α), [$z_{1-0.05}$=1.645]

$$S_{TOT} = \sqrt{S_P^2 + S_A^2 + S_B^2}$$

$S_P$=Pre-analytical standard deviation including dose and test administration variability
$S_A$=Analytical standard deviation
$S_B$=Intra-subject biological variability expressed as standard deviation
RIS=Result Interval Size
For kPCD, RIS=0.1
For Scintigraphy, RIS=1.0

The above calculation is based on a set of assumptions including that $S_P$ and $S_A$ are stable over the required time points, that within-subject, time related biologic variability ($S_B$) is a random, independent fluctuation around a homeostatic set-point and that the $S_{TOT}$ used applies to both the initial and final gastric emptying tests for the individual. It is also assumed that for the GEBT (kPCD), $S_{TOT}$=6.51 for normal and delayed emptying subjects at the 90, 120 and 150 minute time points and that for scintigraphy (% emptied), $S_{TOT}$=7.2 for normal and delayed emptying subjects at the 90, 120 and 150 minute time points.

Example of the calculation of a critical increase, $\Delta_\uparrow$, is provided as follows
For the GEBT (kPCD), 95% Confidence $$\Delta_\uparrow = (\sqrt{2} \times 1.645 \times 6.51) + (1.35 \times 0.1)$$

$$\Delta_\uparrow = 15.3$$

For Scintigraphy (% Emptied)

$$\Delta_\uparrow = (\sqrt{2} \times 1.645 \times 7.2) + (1.35 \times 1)$$

$$\Delta_\uparrow = 18$$

The above calculations can be used to create confidence levels, such as those shown in Table 6.

TABLE 6

| GE Test | Confidence Level | | |
|---|---|---|---|
| | 80% (z = 0.842) | 90% (z = 1.282) | 95% (z = 1.645) |
| GEBT (kPCD) | 7.9 | 11.9 | 15.3 |
| Scintigraphy (% Emp) | 9.9 | 14.4 | 18.1 |

The above confidence levels can be applied to patient data to determine whether a change in results is due to therapy or natural patient variation. For example, referring to Table 4, a patient found to be borderline for delayed emptying with baseline GEBT kPCD at 120 minutes of 40.0 would require a post-therapy kPCD≧55.3 kPCD to indicate a significant change due to therapy with 95% confidence. Similarly, a patient found to be borderline for delayed emptying with a baseline scintigraphic % emptied at 120 minutes of 60% would require a post-therapy % Emptied≧70% to indicate a significant change due to therapy with 80% confidence.

Hence, one can see that to simply dichotomize results as normal or abnormal, e.g., normal vs. slow or normal vs. fast, does not address critical elements of within-subject time-related biologic variation in gastric physiology, nor does it address the clinical reality of overlapping distributions of gastric emptying rates observed in healthy vs. sick patients. Due to the unique nature of measurements of the rate of gastric emptying, omitting these issues from diagnostic categorization methods could lead to diagnostic misclassifications of test results when using a simple dichotomous COP approach. Applicant's diagnostic zone classification system provides a more accurate assessment of a patient's gastric motility status in a manner that is consistent with true gastric physiology and clinical reality.

What is claimed is:

1. A method for assessing a patient's gastric emptying, the method comprising:
   performing a gastric emptying test on the patient;
   obtaining a gastric emptying measurement for at least one desired time point;
   classifying the gastric emptying measurement, the classifying comprising placing the gastric emptying measurement into a zone selected from the group consisting of an abnormal zone, a borderline zone, or a normal zone, wherein the abnormal zone is either a delayed emptying zone or a rapid emptying zone, and wherein each the abnormal zone, the borderline zone, and the normal zone have been developed using gastric emptying measurements and biologic variation measurements from healthy patients, and further comprising placing the gastric emptying measurement into an intra-zone classification within the selected zone.

2. The method of claim 1, wherein the classifying comprises placing the gastric emptying measurement into a zone selected from the group consisting of a delayed emptying zone, a borderline zone, a normal zone, a second borderline zone, and a rapid emptying zone, wherein each the delayed emptying zone, the borderline zone, the normal zone, the second borderline zone, and the rapid emptying zone have been developed using gastric emptying measurements and biologic variation measurements from healthy patients.

3. The method of claim 1, wherein the at least one desired time point includes a 45 minute time point, a 90 minute time point, a 120 minute time point, a 150 minute time point, and/or a 180 minute time point.

4. The method of claim 1, wherein the method comprises classifying scintigraphic test measurements.

5. The method of claim 1, wherein the method comprises classifying breath test measurements.

6. The method of claim 1, wherein the classifying comprises classifying a scintigraphic test measurement at a 45 minute time point, a 90 minute time point, a 120 minute time point, a 150 minute time point, and a 180 minute time point, the classifying further comprising:
  placing the scintigraphic test measurement into: (a) a delayed emptying zone when the scintigraphic test measurement is less than 6.3% emptied, (b) a borderline zone when the scintigraphic test measurement is between 6.3 and 29.9% emptied, or (c) a normal zone when the scintigraphic test measurement is greater than 29.9% emptied at the 45 minute time point;
  placing the scintigraphic test measurement into: (a) a delayed emptying zone when the scintigraphic test measurement is less than 36.2% emptied, (b) a borderline zone when the scintigraphic test measurement is between 36.2 and 62.6% emptied, or (c) a normal zone when the scintigraphic test measurement is greater than 62.6% emptied at the 90 minute time point;
  placing the scintigraphic test measurement into: (a) a delayed emptying zone when the scintigraphic test measurement is less than 56.1% emptied, (b) a borderline zone when the scintigraphic test measurement is between 56.1 and 79.5% emptied, or (c) a normal zone when the scintigraphic test measurement is greater than 79.5% emptied at the 120 minute time point;
  placing the scintigraphic test measurement into: (a) a delayed emptying zone when the scintigraphic test measurement is less than 67.0% emptied, (b) a borderline zone when the scintigraphic test measurement is between 67.0 and 87.8% emptied, or (c) a normal zone when the scintigraphic test measurement is greater than 87.8% emptied at the 150 minute time point; or
  placing the scintigraphic test measurement into: (a) a delayed emptying zone when the scintigraphic test measurement is less than 79.4% emptied, (b) a borderline zone when the scintigraphic test measurement is between 79.4 and 95.6% emptied, or (c)-a normal zone when the scintigraphic test measurement is greater than 95.6% emptied at the 180 minute time point.

7. The method of claim 1, wherein the classifying comprises classifying a breath test measurement at a 45 minute time point, a 90 minute time point, a 120 minute time point, a 150 minute time point, and a 180 minute time point, the classifying further comprising:
  placing the breath test measurement into: (a) a delayed emptying zone when the breath test measurement is less than 6.3 kPCD, (b) a borderline zone when the breath test measurement is between 6.3 and 19.5 kPCD, or (c) a normal zone when the breath test measurement is greater than 19.5 kPCD at the 45 minute time point;
  placing the breath test measurement into: (a) a delayed emptying zone when the breath test measurement is less than 21.9 kPCD, (b) a borderline zone when the breath test measurement is between 21.9 and 44.2 kPCD, or (c) a normal zone when the breath test measurement is greater than 44.2 kPCD at the 90 minute time point;
  placing the breath test measurement into: (a) a delayed emptying zone when the breath test measurement is less than 33.1 kPCD, (b) a borderline zone when the breath test measurement is between 33.1 and 55.3 kPCD, or (c) a normal zone when the breath test measurement is greater than 55.3 kPCD at the 120 minute time point;
  placing the breath test measurement into: (a) a delayed emptying zone when the breath test measurement is less than 39.5 kPCD, (b) a borderline zone when the breath test measurement is between 39.5 and 59.1 kPCD, or (c) a normal zone when the breath test measurement is greater than 59.1 kPCD at the 150 minute time point; or
  placing the breath test measurement into: (a) a delayed emptying zone when the breath test measurement is less than 38.1 kPCD, (b) a borderline zone when the breath test measurement is between 38.1 and 54.9 kPCD, or (c) a normal zone when the breath test measurement is greater than 54.9 kPCD at the 180 minute time point.

8. The method of claim 1, wherein the placing the gastric emptying measurement into an intra-zone classification includes placing the gastric emptying measurement into an intra-zone selected from the group consisting of a high intra-zone, a middle intra-zone, and a low intra-zone.

9. The method of claim 1, further comprising:
  measuring the patient's biological variation;
  calculating a critical increase or a critical decrease using the patient's biological variation, wherein the critical increase indicates how much a gastric emptying measurement must increase in order to reflect a true change in the patient's result, wherein the critical decrease indicates how much a gastric emptying measurement must decrease in order to reflect a true change in the patient's result; and
  performing an additional gastric emptying test on the patient to determine if the critical increase or critical decrease has been reached.

10. A method of treating a patient, comprising:
  performing a gastric emptying test on the patient;
  obtaining a gastric emptying measurement at a desired time point;
  classifying said gastric emptying measurement at said desired time point, the classifying comprising placing the gastric emptying measurement into a zone selected from the group consisting of an abnormal zone, a borderline zone, and a normal zone, wherein the abnormal zone is either a delayed emptying zone or a rapid emptying zone, and wherein the borderline zone is either a delayed emptying borderline zone or a rapid emptying borderline zone;
  selecting a therapeutic action that is correlated to the selected zone, wherein the selecting comprises:
    selecting no action when the normal zone is selected;
    selecting a delayed emptying mild action or a delayed emptying aggressive action when the delayed emptying borderline zone is selected;
    selecting a rapid emptying mild action or a rapid emptying aggressive action when the rapid delayed emptying borderline zone is selected;
    selecting a delayed emptying aggressive action or a delayed emptying very aggressive action when the delayed emptying zone is selected; or
    selecting a rapid emptying aggressive action or a rapid emptying very aggressive action when the rapid emptying zone is selected;
  measuring the patient's biological variation;
  calculating a critical increase or a critical decrease using the patient's biological variation, wherein the critical increase indicates how much a gastric emptying measurement must increase in order to reflect a true change in the patient's result, wherein the critical decrease indicates how much a gastric emptying measurement must decrease in order to reflect a true change in the patient's result; and performing an additional gastric emptying test on the patient to determine if the critical increase or critical decrease has been reached.

11. The method of claim 10, wherein the delayed emptying mild action or the rapid emptying mild action includes adjusting the patient's diet.

12. The method of claim 10, wherein the delayed emptying aggressive action or the rapid empting aggressive action includes administering a pharmaceutical agent to the patient.

13. The method of claim 10, wherein the delayed emptying very aggressive action or the rapid emptying very aggressive action includes performing a surgical procedure on the patient.

14. A display for illustrating gastric emptying results, the display comprising:

a series of time points; and a gastric emptying classification system associated with each time point in said series of time points, the gastric emptying classification system comprising an abnormal zone, a borderline zone, and a normal zone, wherein the abnormal zone is a delayed emptying zone or a rapid emptying zone, wherein each the abnormal zone, the borderline zone, and the normal zone are further associated with an intra-zone classification system.

15. The display of claim 14, wherein the intra-zone classification system comprises a high intra-zone, a middle intra-zone, and a low intra-zone.

\* \* \* \* \*